(12) United States Patent
Jagga

(10) Patent No.: US 10,314,662 B2
(45) Date of Patent: *Jun. 11, 2019

(54) MEDICAL DEVICE CONTROL INTERFACE

(71) Applicant: SYNAPTIVE MEDICAL (BARBADOS) INC., Bridgetown (BB)

(72) Inventor: Arun Victor Jagga, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 14 days.

This patent is subject to a terminal disclaimer.

(21) Appl. No.: 15/803,092

(22) Filed: Nov. 3, 2017

(65) Prior Publication Data

US 2018/0055590 A1   Mar. 1, 2018

Related U.S. Application Data

(63) Continuation of application No. 14/331,484, filed on Jul. 15, 2014, now Pat. No. 9,827,060.

(51) Int. Cl.

| G06F 3/02 | (2006.01) |
|---|---|
| G09G 5/00 | (2006.01) |
| A61B 34/00 | (2016.01) |
| A61B 42/10 | (2016.01) |
| A61B 34/20 | (2016.01) |
| A61B 34/37 | (2016.01) |
| A61B 90/00 | (2016.01) |
| A61B 18/14 | (2006.01) |
| G08C 17/02 | (2006.01) |
| A61B 17/34 | (2006.01) |
| A61B 17/00 | (2006.01) |
| A61B 18/00 | (2006.01) |

(52) U.S. Cl.
CPC .......... *A61B 34/74* (2016.02); *A61B 18/1445* (2013.01); *A61B 34/20* (2016.02); *A61B 34/37* (2016.02); *A61B 34/76* (2016.02); *A61B 42/10* (2016.02); *A61B 90/37* (2016.02); *G08C 17/02* (2013.01); *A61B 17/34* (2013.01); *A61B 2017/00973* (2013.01); *A61B 2018/00595* (2013.01); *A61B 2034/2055* (2016.02); *A61B 2034/2063* (2016.02); *A61B 2034/741* (2016.02); *A61B 2090/373* (2016.02); *A61B 2090/3735* (2016.02); *G08C 2201/32* (2013.01); *G08C 2201/50* (2013.01)

(58) Field of Classification Search
CPC .......... A61B 17/34; A61B 2017/00973; A61B 2034/2055; A61B 2034/741; A61B 34/25; A61B 34/74

See application file for complete search history.

(56) References Cited

U.S. PATENT DOCUMENTS

| 2013/0046302 A1* | 2/2013 | Schneider | A61B 42/10 606/42 |
|---|---|---|---|
| 2013/0226168 A1* | 8/2013 | Ingmanson | A61B 42/10 606/34 |

\* cited by examiner

*Primary Examiner* — Insa Sadio
(74) *Attorney, Agent, or Firm* — Ridout & Maybee LLP

(57) ABSTRACT

An interface component is provided for use with a first glove and a medical equipment component. The interface component comprises at least one switch located on the first glove, where each of the at least one switch provides a control signal to the medical equipment component. The interface component may further comprise a controller coupled to the plurality of switches, a power supply module coupled to the controller, and a wireless communications interface coupled to the controller in communication with a wireless interface of the medical equipment component.

20 Claims, 11 Drawing Sheets

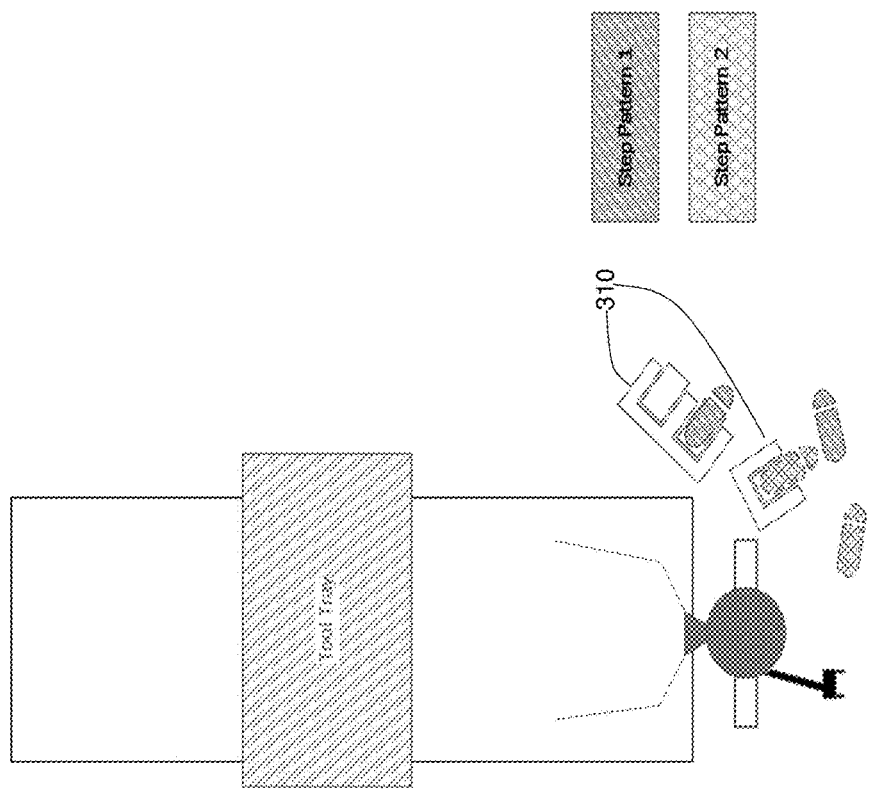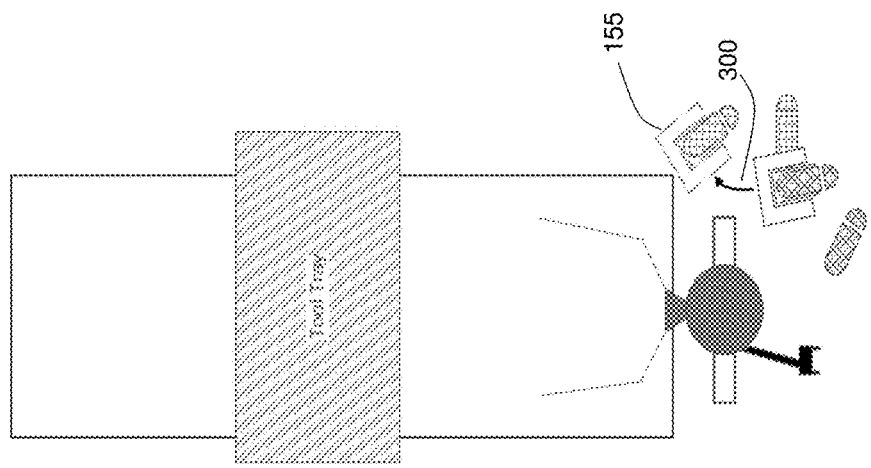
Figure 4

700

| Surgical Tools | | | | | |
|---|---|---|---|---|---|
| Commands | Electrocautery | Drill | Irrigation | Resection | Raman Probe |
| | Activate | On/Off | On/Off | On/Off | On/Off |
| | | Speed | | Speed | Speed |
| | | | | | Area |
| | | | | | Spectrum |

705

| UI Configurations | | | | |
|---|---|---|---|---|
| Commands | Scroll | Scroll Select | Direct Select | Cursor Controller |
| | Next Option | Select Option | Fine Resection Layout | Touch Pad |
| | | | Cannulation Layout | Joy Stick |
| | | | Brightness | Directional Pad |
| | | | T1 or T2 or DTI | |

710

| Exoscope | | | | |
|---|---|---|---|---|
| Commands | Scroll | Scroll Select | Direct Select | Illumination |
| | Next Option | Select Option | NIR Imaging | On/Off |
| | | Activate mode | Hyperspectral Imaging | Increase |
| | | | Visible light Imaging | Decrease |
| | | | Automated Colour Balance | Wavelength band Selection |

715

| Automated Arm | | |
|---|---|---|
| Commands | Actuate | Control |
| | Activate coaxial alignment movement | Directional Pad |
| | Activate cannulation alignment movement | Touchpad |
| | | Joystick |

Figure 7

| Constraints | Under Glove | Integrated into Glove | Over Glove |
| --- | --- | --- | --- |
| Sterilization |  | ● | ● |
| Robustness | ● | ● | ● |
| Dexterity | ● | ● | ● |
| Fatigue of User | ● | ● | ● |
| Tactility | ● | ● | ● |
| Compatibility with Instruments | ● | ● |  |
| Wireless | ● | ● | ● |

Figure 9 ns, displays # MEDICAL DEVICE CONTROL INTERFACE

RELATED APPLICATIONS

The present application is a continuation of U.S. application Ser. No. 14/331,484 filed Jul. 15, 2014, the contents of which are incorporated herein by reference.

TECHNICAL FIELD

The present disclosure is generally related to medical procedures using an access port, and more specifically to a medical device control interface.

BACKGROUND

Port-based surgery allows a surgeon, or robotic surgical system, to perform a surgical procedure involving tumor resection in which the residual tumor remaining after is minimized, while also minimizing the trauma to the intact white and grey matter of the brain. In such procedures trauma may occur, for example due to contact with the access port, stress to the brain matter, unintentional impact with surgical devices, and/or accidental resection of healthy tissue.

Minimally invasive brain surgery using access ports is a recently conceived method of performing surgery on brain tumors previously considered inoperable. To address intracranial surgical concerns, specific products such as the NICO BrainPath™ port have been developed for port-based surgery.

Referring to FIG. 1, the insertion of an access port into a human brain is shown for providing access to internal brain tissue during a medical procedure. In FIG. 1, access port 100 is inserted into a human brain 12, providing access to internal brain tissue. Surgical tools and instruments may then be inserted within the lumen of the access port in order to perform surgical, diagnostic or therapeutic procedures, such as resecting tumors as necessary.

As seen in FIG. 1, port 100 comprises of a cylindrical assembly formed of an outer sheath. Port 100 may accommodate an introducer which is an internal cylinder that slidably engages the internal surface of port 100. The introducer may have a distal end in the form of a conical atraumatic tip to allow for insertion into the sulcal folds of the brain 12. Port 100 has a sufficient diameter to enable bimanual manipulation of surgical tools within its annular volume such as suctioning devices, scissors, scalpels, and cutting devices.

Referring to FIG. 2, an exemplary navigation system is shown to support minimally invasive access port-based surgery. As shown in FIG. 2, a surgeon 103 conducts a minimally invasive port-based surgery on a patient 120 in an operating room (OR) environment. A navigation system 107 comprising an equipment tower, tracking system, displays and tracked instruments assists the surgeon 103 during his procedure. An operator 121 is also present to operate, control and provide assistance for the navigation system 107.

A foot pedal 155 is placed near the surgeon's foot and is utilized to actuate different elements during the procedure. For example, foot pedal 155 may be used to lift or lower the surgical bed, or control zoom of the navigation system 107 or tracking system. In certain instances, multiple foot pedals may be deployed.

Conventional foot pedals used by a surgeon during a surgical procedure, particularly when multiple foot pedals are used, can be a distracting and menial task, given the surgeon must sometimes remove his focus from the surgical field of interest, resulting in the surgeon having to reorient himself when his attention is returned. Therefore, there is an opportunity for improvement in the area of surgical controls. Thus, there is a need for mechanism to provide improved functionality and replacement of the foot pedal.

SUMMARY

One aspect of the present description provides an interface component for use with a first glove and a medical equipment component. The interface component comprises at least one switch located on the first glove, where each of the at least one switch provides a control signal to the medical equipment component. The interface component may further comprise a controller coupled to the at least one switch, a power supply module coupled to the controller, and a wireless communications interface coupled to the controller in communication with a wireless interface of said medical equipment component.

In one example, the first glove includes a surgical glove and the interface component is integrated into the surgical glove. In another example, the first glove is designed to be used with a second surgical glove and the first glove is wearable underneath the second surgical glove. In yet another example, the first glove is designed to be used with a second surgical glove and the first glove is wearable over top of the second surgical glove.

Another aspect of the present disclosure provides an interface component for use with a surgical glove and a medical equipment component. The interface component comprises at least one switch located on the interface component, each of the at least one switch providing a control signal to the medical equipment component. The interface component is wearable on a hand of a surgeon either over top of or underneath the surgical glove.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 4 illustrates various foot pedals and foot positioning of surgeons during commonly performed neurosurgeries;

FIG. 7 shows a number of tables describing input commands for exemplary surgical instruments that can be coupled with the surgical glove interface shown in FIG. 5;

FIG. 9 is a chart illustrating features of various embodiments of the surgical glove interface when used in a surgical context;

DETAILED DESCRIPTION

Figure 1:
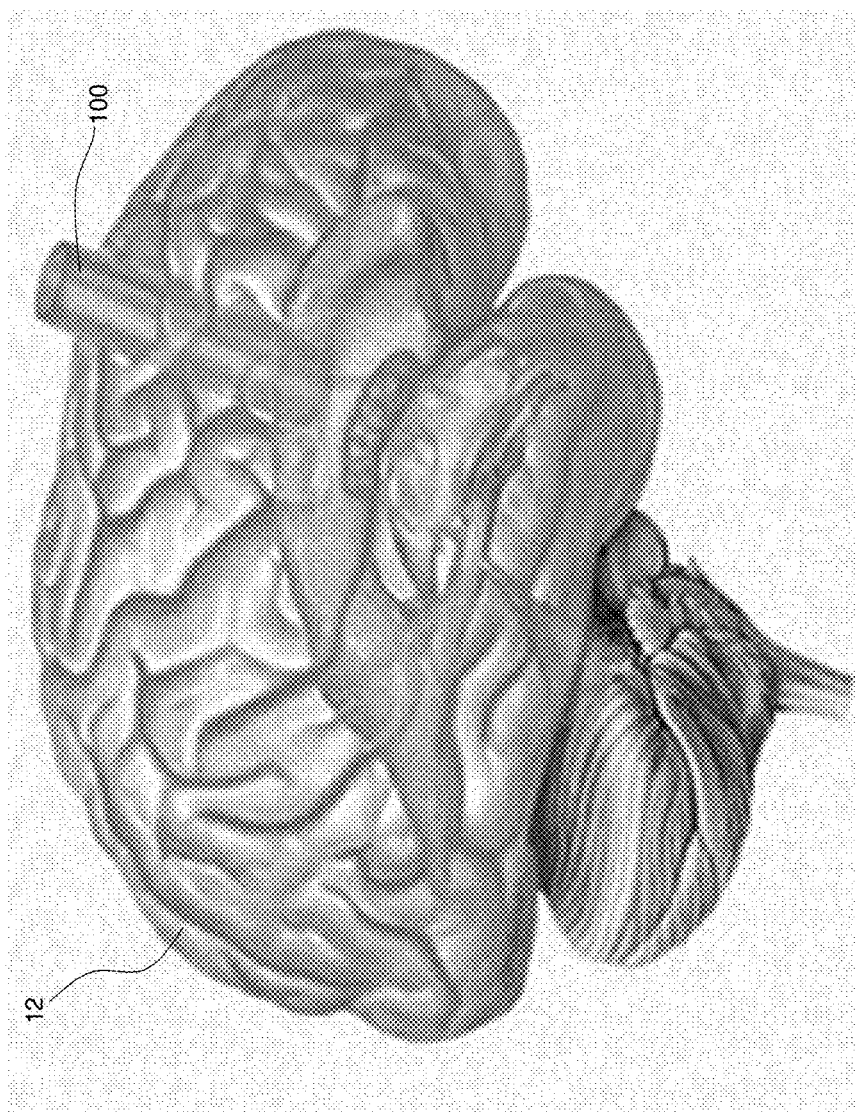
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

The use of switches in presently performed surgical procedures is a useful feature for convenient control of the surgical devices and systems involved. However, presently available actuation devices result in inefficiencies that must be overcome by the surgeon and/or surgical team. Examples of such inefficiencies will be described below.

There are many sources of ergonomic issues encountered during common thoracic surgeries shown using foot pedals. The use of foot pedals creates problems associated with physical, perceptual, and cognitive use. The present application aims to address these problems and others associated with presently used actuation or control devices.

In an ideal surgical procedure, a surgeon will minimize the amount of time in which his focus is away from the surgical site of interest. This includes minimizing the time during which the surgeon is not viewing the surgical site of interest as well as the time during which the surgeon is not in the bimanual procedural position or any other potential instance which can be avoided to minimize the time required for the surgery. When utilizing a foot pedal switch as described above, inefficiencies can be attributed to the situations described below.

Figure 3:
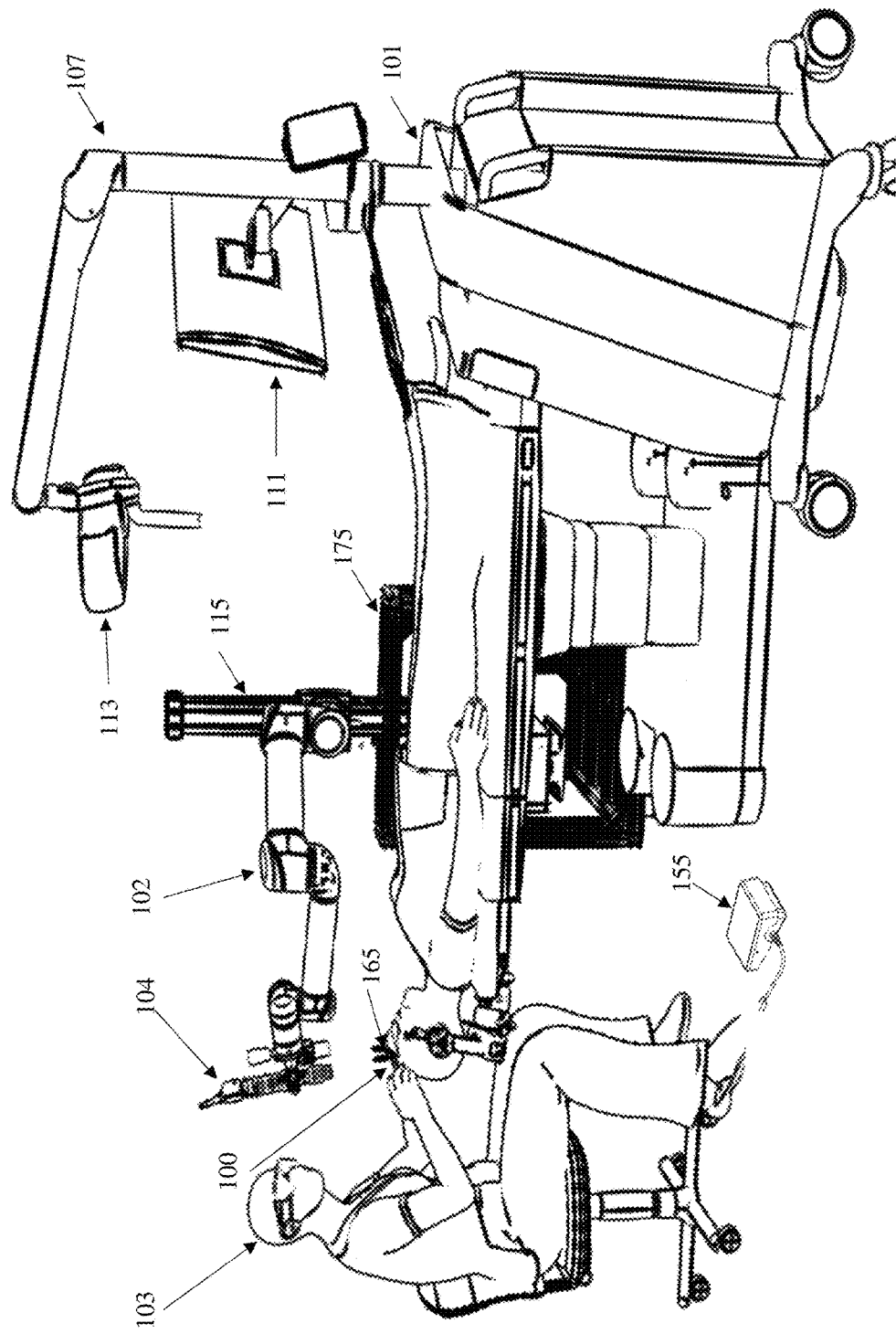
FIG. 3 is a diagram illustrating components of an exemplary surgical system used in port based surgery.

Referring now to FIG. 3, a diagram is shown illustrating components of an exemplary surgical system such as the medical navigation system 107 used in port based surgery. Reference is also made to FIG. 4, which shows various foot pedals and foot positioning of a surgeon during commonly performed surgeries. In one instance the surgeon may have to reposition one or more foot pedals 155 when he changes his orientation relative to the patient during surgery, indicated by reference 300 (FIG. 4). When this occurs, the surgeon's focus is removed from the surgical area of interest to correctly reposition the foot pedal 155. In addition, this may also require the surgeon to remove his tools from the bimanual procedural position as well.

During a medical procedure a surgeon may have to use the foot pedals 155 in an inopportune (e.g., non-ergonomic) position. Various operating stances can require the surgeon to position himself awkwardly and therefore make the use of a pedal inefficient and difficult to do with accuracy. In one example, the surgeon may be leaning over the patient requiring the surgeon to fully extend his leg and even have to stand on his toes. It is apparent that in such a stance the resulting positioning of the foot would make it difficult for the surgical personnel to operate the foot pedal because in such a position the heel of the foot would be elevated from the ground. Even if the foot is located on the ground, but is fully extended, the ball of the foot will be difficult to use in a flexion as it would be required for stability of the surgeon. Therefore, using the foot to operate the foot pedal in such a position would reduce the amount of precision when engaging the foot pedal through a plantar flexion movement. This situation may also require the surgeon to move the pedal(s) 155 positioning on the floor of the operating room resulting in increased time required for the surgical procedure and hence decreasing efficiency of the operation.

The surgeon may also have to use multiple foot pedals 155 during a surgical procedure requiring him to differentiate between foot pedals through proprioception, estimated foot pedal placement knowledge, and his sense of touch as opposed to knowing with a greater certainty the location of the pedal 155 he wants to actuate relative to his foot position. This estimation of pedal 155 location using touch and proprioception may also be inhibited by the wearing of shoes. If the surgeon is unable to locate the pedal 155 using the three senses mentioned, the surgeon will be again required to remove his focus from the surgical site of interest and his tools from the bimanual procedural position in order to do so. It should be noted that this is a consequence of free placement of the pedals 155 on the floor, since the pedals 155 aren't placed at a "known" relative position (e.g., a position relative to the surgical bed or area of interest) that the surgeon could intuitively find using touch or proprioception knowledge in combination with previous surgical experience. Other issues in locating and engaging the foot pedal(s) 155 may be caused when the foot pedal 155 is placed under the surgical bed, where it would be out of site of the surgeon and may require the surgeon to spend more time locating the pedal(s) 155 as opposed to being positioned in clear site.

At points during the surgery the surgeon may have to stand and utilize motor functions in both his arms and legs to position a medical device and actuate it simultaneously using the foot pedal 155 respectively. This may be an inefficient way for the surgeon to operate a device as the simultaneous actuation of a foot pedal 155 and precise arm movement is not an intuitive function for most individuals.

The use of a foot pedal 155 in a surgical procedure may also impose additional wiring on the floor of the surgical suite, resulting in increased tripping hazards in the operating room, which are dangerous and may cause serious harm to the patient if surgical personnel were to trip over such wiring.

An alternate procedural element actuation device utilizes a tool with an attached or integrated switch such as the Stryker Smart Instruments. When using such a tool, inefficiencies may occur in the following contexts. The tool may have a limit on its available area for a given user interface control containing switches for manipulation of elements used during the surgical procedure. Reasons for such limits relate to the user interface being integrated into the tool as opposed to a separate control user interface. Since surgical tools are precise instruments to be manipulated by the surgeon, their weights, sizes, and overall features greatly affect the dexterity of the surgeon. Therefore, increasing the size of the user interface control area for more numerous and/or larger more easily identifiable and accessible buttons may result in heftier instruments again reducing the precision of the surgeon when using the tool. Additionally, when tools are engaged in minimally invasive surgeries, the tools must be manipulated within a small corridor. In this context increasing the size of the tool may not be feasible as it may occlude the view down the corridor or become too large as to restrict access of the tool into the corridor. Alternate issues are associated with placing an electronic user interface on a surgical tool. The electronics must be designed to withstand commonly used sterilization processes. Viable ways of achieving such an ability to withstand sterilization require the electronics to be bulkier and heavier than their non-integrated counterparts (e.g., the tool without the user interface controller) as sterilization occurs at high temperatures and pressures. Specifically, when sterilizing medical instruments using the autoclaving technique the instruments must withstand temperatures of 121 C-190 C and pressures of 15 psi-40 psi.

The manufacture and purchase of tools with built in user interfaces is also problematic. Multiple surgical tools each having a built in user interface (UI), for example, both a resection tool and bipolar pituitary forceps, to be used within a surgical procedure will likely be more costly than having a single surgical glove interface that can be integrated with all potential tools the surgeon may use. An advantage to using a single entity surgical glove interface disclosed herein is that the surgical glove interface may be configured to adaptively switch output selection such that the detection of the tool being used by the system sets the output of each of the buttons, as opposed to having a separate user interface on each medical tool as would be required by a surgical tool with a built in user interface.

When utilizing a kinect based gesture control user interface to control surgical procedural elements, inefficiencies can occur in the following contexts. Such a user interface control requires the surgeon to remove his hands from the bimanual procedural position when performing the gestures required to control the user interface. In addition to this requirement, the surgeon must perform an initial gesture to initiate the Kinect sensors and begin controlling the user interface which in turn increases the time required for the surgery as opposed to being able to constantly control the interface. A consequence of this user interface control system is that the surgeon has to remove his attention from the surgical site of interest (or equivalently a display of the surgical site of interest) when performing gestures to control the system. This results in the surgeon having to directionally reorient himself with the display of the surgical site of interest with respect to the spatial orientation of the patient in the operating room when returning to the bimanual procedural position, which will also result in an increase of the total time of the surgical procedure. Since the Kinect sensor is a detector with an inherent field of view, the surgeon may additionally have to reposition himself away from his surgical procedural stance in order to enter the correct field of view, to gain full control over the functionality of the user interface.

Referring back to FIG. 3, FIG. 3 illustrates a medical navigation system 107 having an equipment tower 101, a tracking system 113, a display 111 (e.g., to show a graphical user interface), an intelligent positioning system 175 and tracking markers 165 used to track medical instruments or an access port 100. Tracking system 113 may be considered an optical tracking device or tracking camera.

In FIG. 3, a surgeon 103 is performing a tumor resection through a port 100, using an imaging device 104 to view down the port at a sufficient magnification to enable enhanced visibility of the instruments and tissues. The imaging device 104 may be an exoscope, videoscope, wide field camera, or an alternate image capturing device. The imaging sensor view is depicted on the visual display 111 which the surgeon 103 uses for navigating the port's distal end through the anatomical region of interest. The foot pedal 155 is located in an accessible vicinity to the surgeon's foot and is utilized to actuate an element used in the procedure.

The intelligent positioning system 175 receives as input the spatial position and pose data of the automated arm 102 and target (for example the port 100) as determined by tracking system 113 by detection of the tracking markers 165 on a wide field camera and the port 100.

The foot pedal 155 is located in an accessible vicinity to the surgeon's foot. Foot pedal 155 may be used to actuate an element used in the procedure such as a neurosurgical drill, an illumination source, automated arm movement, a UI configuration, a resection device, an irrigation device, an imaging procedure, an imaging acquisition, a change of phase during surgery, or any other element requiring actuation during a surgical procedure. Foot pedal 155 may have multiple activation input configurations or modes as described in the following examples.

A first input configuration (or first mode) includes a binary switch mode in which a press of foot pedal 155 causes the foot pedal 155 to output a signal which actuates the state of a procedural element from "on" to "off" position. A second input configuration (or second mode) is a variable switch mode in which the output signal of the foot pedal is proportional to the degree of force applied to the pedal by the user. A third input configuration (or third mode) may be a multiple switch mode in which a press of the foot pedal cycles the element through various modes of function (i.e. modes of function of the element). It should be noted that all switches mentioned in this disclosure can be formed of any mechanism to allow for control of or actuation of a device.

These input configurations can also be implemented in combinations provided the system utilizes more than one foot pedal as shown as 310 in FIG. 4. For example, given two foot pedals as shown in FIG. 4, combinations can be two binary switches, in which the combined activation of both foot pedals can result in an alternate output from the output of each foot pedal activated individually. Another example combination using two foot pedals can be two multiple switch modes in which the foot pedal outputs when both are activated can be different from when the pedals are activated individually. Another example using two foot pedals would be a binary switch and a multiple switch in which the output of the activation of both foot pedals may be different than when the pedals are activated individually.

According to one aspect of the present description, a surgical glove interface described herein allows a surgeon to increase the efficiency of surgical procedures using the presently available tools and systems.

Figure 5:
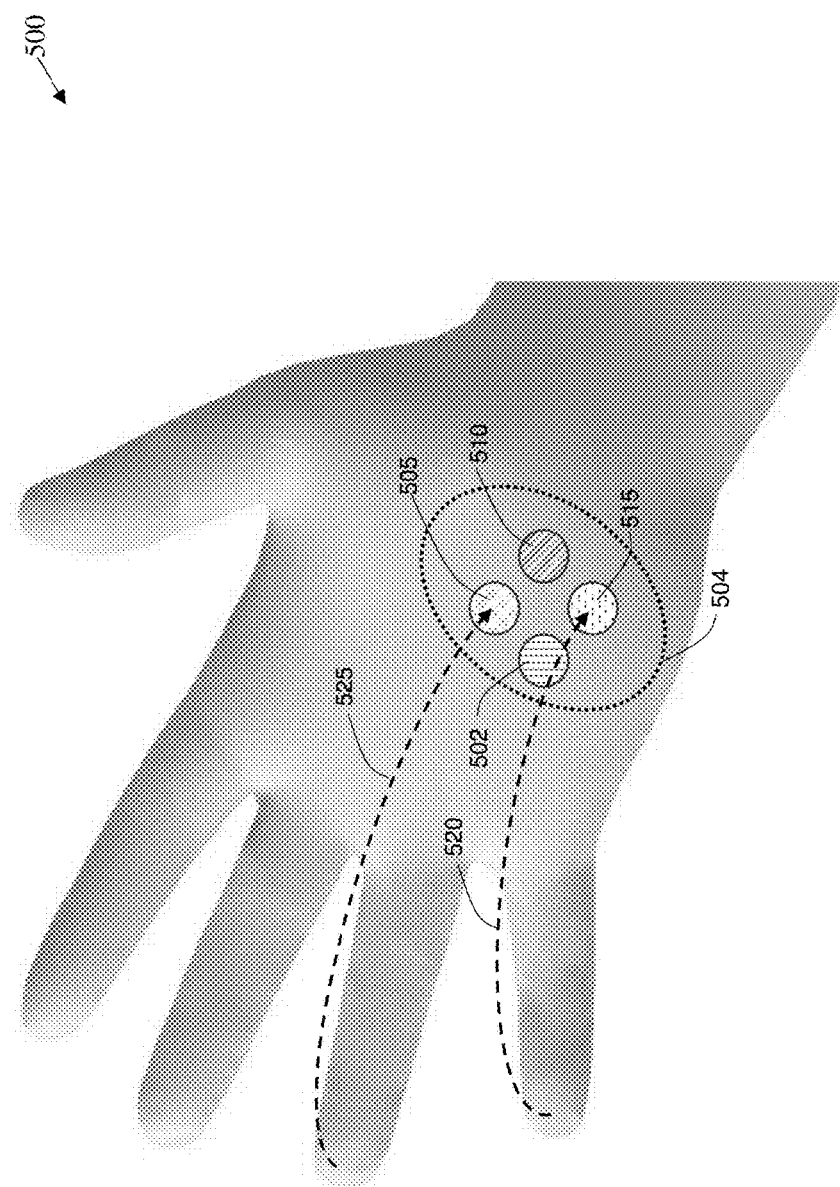
FIG. 5 illustrates an exemplary surgical glove interface.

Referring to FIG. 5, an exemplary surgical glove interface 500 is shown according to one aspect of the present disclosure. The surgical glove interface 500 aims to provide a more efficient user interface control than those mentioned above, which may take advantage of the bimanual procedural position and commonly used finger positioning of a surgeon holding a surgical tool.

Typically, when performing a surgery, the surgeon's pinky and ring finger are located near the palm, while the thumb index and middle fingers are used to manipulate the tools on both hands. Given the pinky and ring fingers are free, the glove can be situated with a user interface positioned on the palm, as shown by reference 504, to allow the free fingers to press switches of the surgical glove interface 500, as illustrated by arcs 520 and 525.

FIG. 5 depicts an exemplary embodiment of such an interface where the switches of the interface are integrated into the glove at the positioning where the ring and pinky fingers are located during surgery in region 504 during three finger bimanual manipulation of surgical tools. In FIG. 5, the switches are formed of four buttons (502, 505, 510, and 515), which in one example may each have an individual tactile pattern for easier differentiation.

The use of the surgical glove interface 500 may eliminate the need for the surgeon to utilize his eyes to locate a switch, such as in the case of foot pedals and the tool integrated controller user interface as described above, as the controller of the surgical glove interface 500 may be located in an easily accessible vicinity to the surgeon's ring and pinky fingertips throughout the performance of the surgery. This makes determining the position of the interface and associated switches 502, 505, 510, 515 simply a matter of using the proprioception sense. In contrast, both the use of the foot pedal and the tool integrated user interface would require the surgeon to estimate the relative location of the switches on the foot pedal and the tool respectively relative to the engaging body part (e.g., the surgeon's foot and finger(s) respectively) in addition to using proprioception. The use of the surgical glove interface 500 may also substantially reduce or eliminate the need for the surgeon to retract the tools from the bimanual procedural position prematurely during the surgery to allow for control of the user interface, such as when using the Kinect user interface controller.

A disadvantage of a tool integrated user interface controller is that it may require the surgeon to alter his finger positioning to engage the relevant switches while performing surgery. This may reduce the surgeon's precision with the tools as the finger positioning is not optimized for dexterity. In contrast, the surgical glove interface 500 depicted in FIG. 5 does not require the surgeon to substantially alter his finger positioning to engage the relevant switches 502, 505, 510, 515 while performing surgery. It should be noted that this positioning involves using the index finger, middle finger, and thumb to manipulate the tool while the ring finger and pinky fingers are retracted into the palm. The advantage of utilizing the surgical glove interface 500 is important as it allows the surgeon to freely manipulate the tools with maximized precision, as opposed to manipulating the tools with inopportune finger positioning as in the conventional solutions. The location of the region 504 of button interface depicted in FIG. 5 is aimed to be an ergonomic position and hence also allows the surgeon to remain comfortable throughout the procedure reducing fatigue in the surgeon's hands while providing gains of in-hand control of procedural elements.

The use of the surgical glove interface 500 may be implemented for multiple tools in a single surgical procedure where the surgical glove interface 500 configuration will change depending on what tools are used. This may make the surgical glove interface 500 a more economically viable option than having multiple tools with integrated user interface controllers.

As mentioned above, having a tool integrated user interface controller decreases the tools precision as a result of various dimensional considerations such as size of an access corridor in a minimally invasive surgery, increased dimensions of the tool, such as weight, height, length, width, etc. In contrast, when using the surgical glove interface 500, the interface is situated on the palm of the surgeon, and therefore adding or reducing the features of the interface, such as a touch pad (described below), buttons, etc., do not affect the precision of the tool being used. In addition, the palm of a surgeon will generally have more available space in comparison to a surgical tool handle (e.g., without integrated user interface controller) allowing for a larger user interface controller area.

When presently performing surgery many surgeons utilize a foot pedal while simultaneously maneuvering their surgical tools in the surgical area of interest, for example when resecting a tumor a surgeon will control the removal rate of the resection device with his foot and the resection device's position in the surgical area of interest with his hand, inclusive of the arm. In general, a surgeon's fingers are more agile and precise in applying force than his foot. The surgical glove interface 500 takes advantage of this fact and allows both the positioning of the tool and its control user interface to be managed by the hand of an individual surgeon. Also, since the surgical glove interface 500 is not located on the ground, the additional hazardous wiring mentioned above will be alleviated in the operating room.

Figure 2:
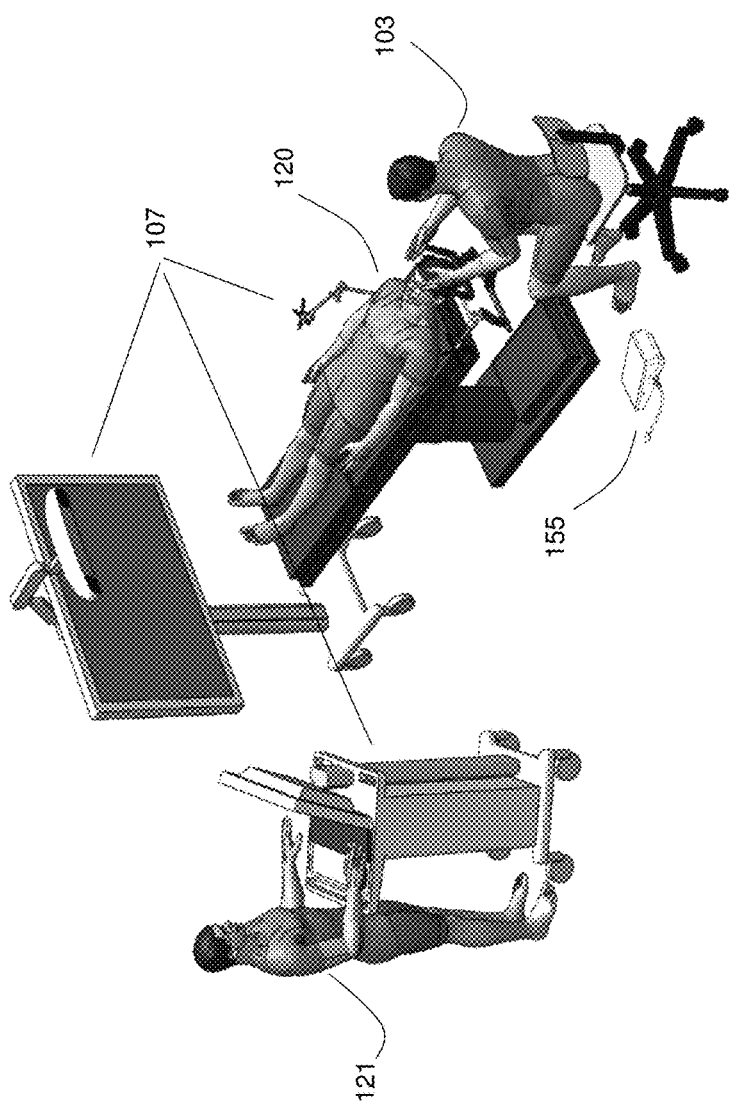
FIG. 2 shows an exemplary navigation system to support minimally invasive access port-based surgery.
Figure 6:
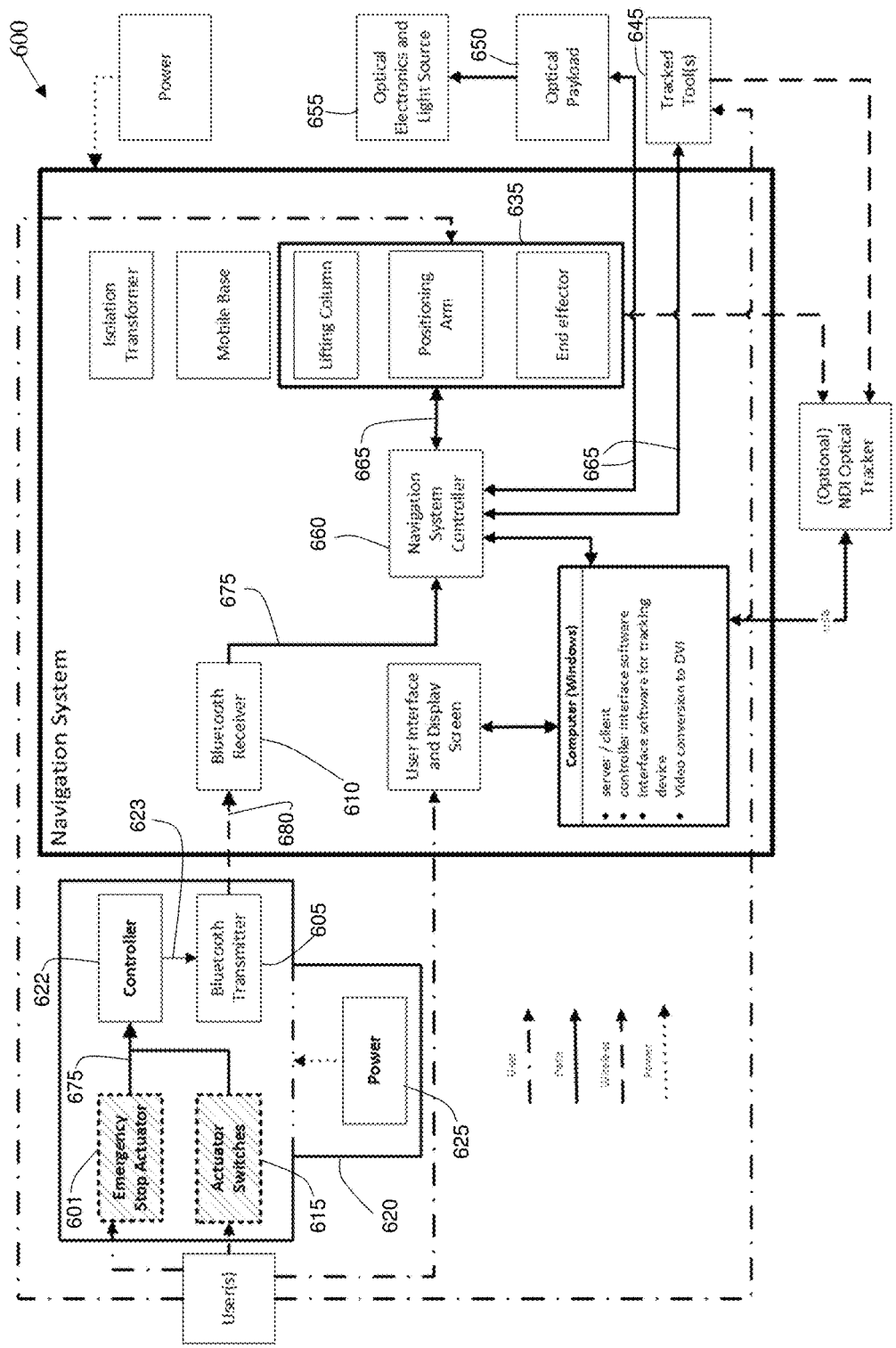
FIG. 6 is block diagram showing an exemplary navigation system or surgical system which may be used with the surgical glove interface shown in FIG. 5.

Referring to FIG. 6, a block diagram is shown illustrating an exemplary medical navigation system 600 that may be used in the systems shown in FIGS. 2 and 3, and may also be used with the surgical glove interface 500 shown in FIG. 5. An example embodiment of a medical navigation system 600 inclusive of an exemplary surgical glove interface 500 disclosed herein is provided in FIG. 6 in a block diagram. The exemplary surgical glove interface 500 is illustrated by reference 620 in FIG. 6. Surgical glove interface 620 (also referred to hereafter as an interface component 620) contains a controller 622, emergency stop 601, switches 615, power source or power supply module 625, and a wireless communications interface 605 (which, in one example, maybe a Bluetooth transmitter). The exemplary power supply module 625 may be portable and rechargeable and may be connected to each of the other exemplary components of the interface component 620. The exemplary surgical glove interface 620 may function in the manner described as follows.

When the switch 615 is triggered, switch 615 provides a control signal 675, which corresponds to a command to the controller 622. The controller 622 then encodes the control signal 675 into a digital signal 623 and relays this digital signal to the wireless communications interface 605. This signal is then encoded and relayed by the wireless communications interface 605 over a radio frequency wireless communication channel 680 using, for example, Bluetooth protocol. The output signal is then received by a wireless interface 610, which in one example may be a Bluetooth transceiver employing the Bluetooth protocol, and is decoded and relayed to the medical navigation system controller 660. The medical navigation system controller 660 then reads the control signal 675 and outputs the corresponding control signals 665 to the various devices used in the medical procedure. While a Bluetooth protocol is provided as an example, any suitable wireless communications system and protocol may be used to meet the design criteria of a particular application, such as Wi-Fi, irDA, or any other suitable system and/or protocol.

The medical navigation system 600 may further interface with tracked tools 645 and control optical electronics or light sources 655 using control signal 665 provided to the optical payload 650.

Examples of various devices 635 and their exemplary command inputs are depicted in the charts shown in FIG. 7 and are described in detail as follows. Chart 700 describes exemplary surgical glove interface 500 output commands that can be used to control the listed surgical tools. An exemplary surgical tool that is commonly utilized in surgery is the bipolar forceps (e.g., electrocautery device), with which a surgeon is able to cauterize vital blood vessels to prevent excessive bleeding. A command that can be actuated using the surgical glove interface 500 (e.g., as depicted in FIG. 5) would be to activate the forceps for cauterization, such as by applying a voltage across the separated tips. A second commonly used surgical tool would be a resection device. The surgical glove interface 500 can be used to implement commands to this device such as the implemented suction force and whether the device is in tissue removal mode (e.g., tissue removal blade activated) or tissue manipulation mode (e.g., tissue removal blade deactivated). The suction force command will determine at what rate tissue will be resected by the device while the removal mode command will indicate to the device to cut the tissue or not. The resection tool commands are analogous to the third surgical tool, the neurosurgical drill, which may also be controlled by the surgical glove interface 500 by the surgeon. Commands for this device may turn the drill on and off and may also dictate the speed of the drill as to minimize trauma to the patient in the form of vibrational pressure and increase the drill's effectiveness. Another exemplary surgical tool that may be controlled by the surgical glove interface 500 is a Raman imaging probe. The surgical glove interface 500 may send commands via the various controllers 622, 660 to this device to dictate its acquisition rate, its acquisition area, its acquisition wavelength band, and when it acquires data.

Referring now to FIG. 7, a number of tables are shown describing input commands for exemplary surgical instruments that can be coupled with the surgical glove interface 500 shown in FIG. 5. Chart 705 in FIG. 7 describes specific surgical glove interface 500 output commands that can be implemented by the medical navigation system 600 graphical user interface (GUI). These commands have various functions that can allow the surgeon to remotely manipulate, navigate, and utilize the GUI without having to remove tools from the bimanual procedural position. The four exemplary commands depicted in the chart will be described in more detail as follows. The first command, scroll, can be used to scroll through various menus on the UI such as "Choose Display Image", "Display Options", "Display Configurations", "Next Phase", etc. These various options can be chosen using the scroll select command, and may result in an additional drop down menu that can be scrolled through and selected using the same system of commands (i.e. scroll and scroll select). An example additional drop down menu for "Display Options" may be comprised of the following options "Brightness", "Contrast", "Colour Balance", etc. and can be used to configure the picture properties displayed on the screen. Additional commands that can be implemented by the surgical glove interface 500 can be used to directly actuate the GUI to execute an option or configuration. Given a surgical glove interface 500 such as depicted in FIG. 5, each button may be used to actuate a different option or configuration of the GUI directly. For example, buttons 505 and 510 may be used to configure the GUI in "Fine Resection Phase" and "Cannulation Phase" layouts as predetermined by the system. For example, in the "Cannulation Phase" layout the GUI may automatically display the depth that the port 100 is penetrated into the brain. The alternative buttons 502 and 515 may be used to directly auto adjust the brightness of the display and scroll through displayed images such as a T1, T2, and DTI.

In addition to or in place of the buttons 502, 505, 510, 515 shown in the surgical glove interface 500, a joy stick, touch pad, directional pad, or scroll pad may be used on the surgical glove to allow the user to navigate the GUI using a cursor as opposed to iteratively scrolling through options using a button switch.

Chart 710 describes specific surgical glove interface 500 output commands that may be used to control an imaging device 104 (FIG. 3). These commands have various functions that can allow the surgeon to manipulate and configure the imaging device to acquire desired intraoperative imaging, without having to remove his tools from the bimanual procedural position at the surgical area of interest. The four exemplary commands depicted in the chart will be described in more detail as follows. The first command scroll can be used to scroll through various options of the imaging device such as "Zoom", "Imaging Mode", "Illumination", "Next Phase", etc. These various options can be chosen using the scroll select command, and may result in an additional drop down menu if selected that can be scrolled through and selected using the same system of commands. An example additional drop down menu for "Imaging Mode" may be comprised of the following additional options "Visible", "NIR", "Hyperspectral", etc. If any of the mentioned exemplary drop down menu commands are selected the imaging device will begin to image in the selected mode. Additional commands that can be implemented by the surgical glove interface 500 can be used to directly actuate the imaging device to execute an option or configuration. For example, buttons 505, 510, and 515 shown in FIG. 5 may be used to directly configure the imaging device in "NIR", "Hyperspectral", and "Visible Light" imaging modes as predetermined by the system. The alternate button 502 may be used to directly automatically adjust the illumination spectrum to optimize the colour balance.

Chart 715 describes specific surgical glove interface 500 output commands that can be used to control an automated arm 102 (FIG. 3). These commands have various functions that can allow the surgeon to manipulate and configure the automated arm to mobilize in a particular manner of movement, without having to remove the tools from the bimanual procedural position at the surgical area of interest. The two exemplary commands depicted in the chart will be described in more detail as follows. The first command actuate can be used to scroll through two movement options listed as "Coaxial Alignment" and "Cannulation Alignment". These movement options will result in the automated arm coaxially aligning with the port 100 or aligning at a predetermined angle to the port 100 optimized for cannulation into the brain respectively. The second command "control" can be used to manually position the arm through the use of a controller located on the surgical glove interface 500, such as a joystick, a directional pad, or a touch pad.

In another example, the switches 502, 505, 510, 515 may be manufactured with physical patterns that can be used to differentiate between the buttons using touch, for example a textured surface for tactile identification by a wearer. In the example depicted in FIG. 5, the buttons 502, 505, 510, and 515 were produced with physical patterns that can be used to identify, through the sensation of touch, each button uniquely. This is advantageous because it allows the surgeon to readily determine which button he is pressing with reduced chance of the surgeon removing his visual focus from the surgical site of interest because the buttons 502, 505, 510, and 515 are strategically placed so the buttons 502, 505, 510, 515 may be easily located using proprioception and easily identified given the patterns render them differentiable through the sensation of touch.

Figure 8:
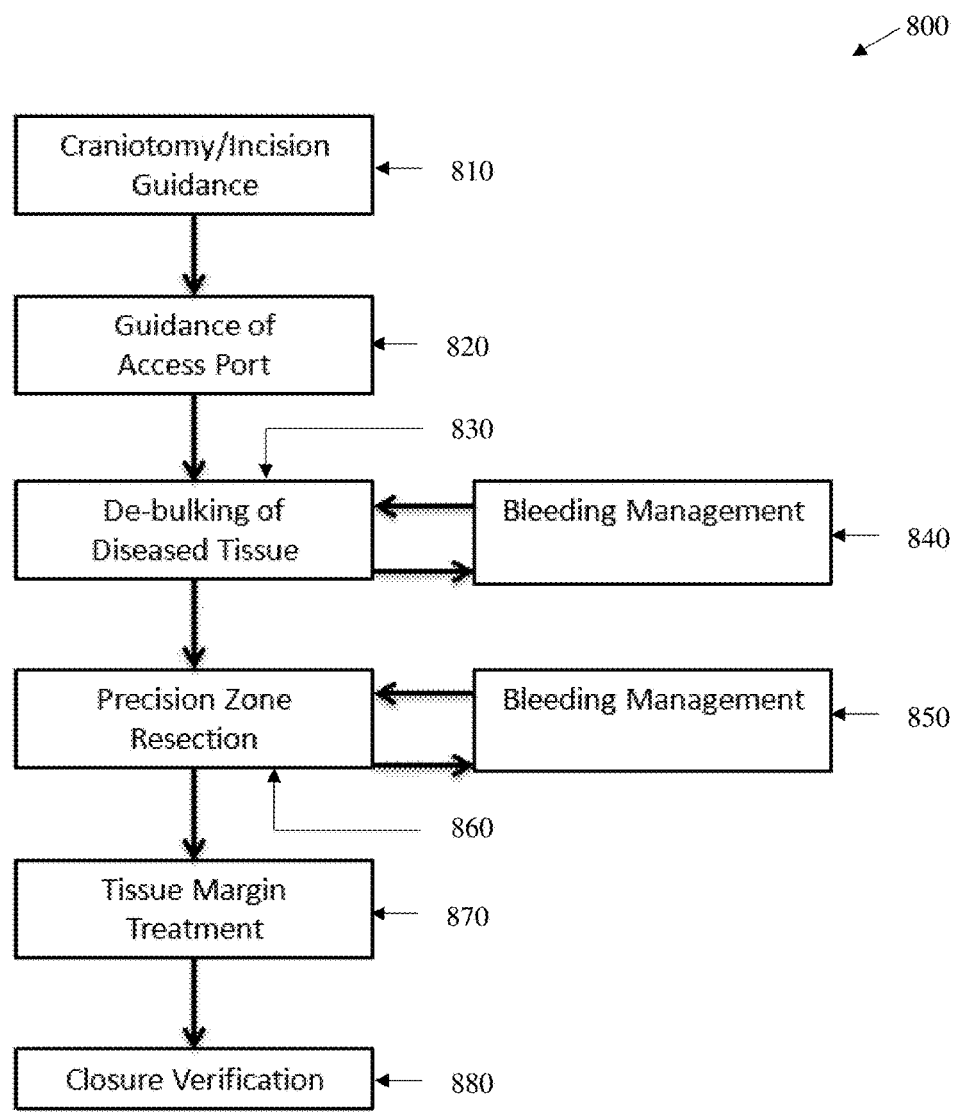
FIG. 8 is a flow chart describing the general steps in a port based neurosurgical procedure.

Referring to FIG. 8, a flow chart is shown describing a method 800 illustrating the general steps in a port based neurosurgical procedure. An example phase breakdown of the port based surgical operation mentioned is shown in FIG. 8. A description of an exemplary surgical glove interface 500 corresponding applicability in each of the phases is provided below. The description exemplifies the use of the surgical glove interface 500 in streamlining the surgical process during each phase.

At 810, the first phase in the port based neurosurgical procedure is the incision of the scalp and craniotomy. During this stage, the surgical glove interface 500 depicted in FIG. 5 can be implemented to control the neurosurgical drill. Exemplary commands provided by the surgical glove interface 500 to be configured with the drill are shown in chart 700 in FIG. 7 and described above in further detail.

At 820, once the incision and craniotomy are completed, the surgery enters the "Guidance of Access Port" phase and the surgical glove interface 500 can be implemented to control the automated arm 102 (FIG. 3). During this phase the port is penetrated into the brain until it reaches the target (e.g., usually a tumor) depth. Exemplary commands the surgical glove interface 500 may be configured to provide to the automated arm are shown in chart 710 in FIG. 7 and are described above in further detail. One specific command relevant to this phase of the surgery may be "Activate cannulation alignment movement". This command when activated by the surgeon will cause the automated arm to align at such a position to allow the imaging device to view the cannulation of the port at an angle. This would expose the graduation marks on the port to the surgeon to inform him of the depth of the port penetrated within the brain.

In the next phases 830 and 840, which are usually simultaneous, the surgical glove interface 500 shown in FIG. 5 may be used to aid in both the resection control during gross de-bulking of unhealthy brain tissue as well as imaging control in case an alternate imaging modality may be required. During these steps, the surgeon 103 may activate the surgical glove interface 500 to control a resection tool suction speed when resecting unhealthy tissue, as shown in chart 700 in FIG. 7. An exemplary resection tool is the Myriad™ produced by NICO. An additional control the surgeon has over a resection tool is the ability to activate and deactivate the device as required. The second simultaneous step in this procedure is managing any bleeding that may occur within the surgical area of interest. During surgery a common occurrence is the rupturing of a blood vessel. If such a situation occurs, heavy bleeding precedes it, which can be problematic for viewing the surgical area of interest and closing the wound accordingly. The surgical glove interface 500 can be utilized in this situation to configure the imaging device to utilize near infrared (NIR) imaging. The advantages of NIR imaging when viewing blood is its increased penetration depth in blood, rendering it more transparent when compared to imaging using visible light.

After the bulk resection phase the surgical procedure enters the next two phases of fine-resection 860 and bleeding management 850, which are usually done simultaneously. In these phases, the surgeon removes the tumor from the fringes of healthy tissue, by differentiating, using his knowledge, between the healthy and unhealthy tissue. During fine-resection, the surgical glove interface 500 may be configured to implement the Raman probe surgical tool to acquire spectrums and utilize the spectrums to differentiate more effectively between healthy and unhealthy brain tissue at the boundary of a tumor 102, for example. Exemplary commands of such a device are provided in chart 700 in FIG. 7 and described above in further detail. Another tool that can be actuated using the surgical glove interface 500 to manage bleeding once the source is located is the electrocautery tool. This tool can be used to cauterize a blood vessel or other bodily tissue to effectively close the wound. Exemplary commands that can be integrated into the surgical glove interface 500 for this tool are also depicted in chart 700 in FIG. 7 and are described above in further detail.

At 870, the next phase of surgery, tissue margin treatment involves delivering therapeutic agents to the surgical site to treat any remaining unhealthy tissue in the area and assure an optimal recovery of the patient. The surgical glove interface 500 may be implemented in this step to control a device to deliver a therapeutic solution. In this example, the surgical glove interface 500 may be used to configure the device to deliver a specific type of therapeutic solution. In another example, the surgical glove interface 500 may be used to control the GUI to create a mixture of the correct solution similar to a user interface control device such as a computer mouse.

At 880, the final step involves the removal of the port and closure of the wound in addition to the application of materials to assist in healing the surgical area. In this step the surgical glove interface 500 may be used to control an irrigation device to clean the surgical area of interest before the surgeon exits. Exemplary commands that can be integrated into the surgical glove interface 500 for this tool are provided in chart 700 shown in FIG. 7 and are described above in further detail.

While a number of examples of commands are provided that can be implemented using the surgical glove interface 500, the controller 622 and the medical navigation system 600 can be configured to implement any suitable control configuration for any number of medical tools or equipment according to the design criteria of a particular application.

While the surgical glove interface 500 described above allows for improved efficacy of surgical procedures, instruments in the surgical suite should adhere to minimum standards and requirements to be implemented safely. In particular, there exist design considerations that must be taken into account to allow for the glove 500 to improve the efficacy of surgical procedures as mentioned.

Referring to FIG. 9, some exemplary non-limiting considerations are provided in the table 900. In particular, the interface 500 to be applied to a surgical glove may be integrated: (a) on top of a presently used surgical glove, (b) into a surgical glove, or (c) below or underneath a surgical glove.

The first row of the table 900 refers to the need to sterilize the surgical glove interface 500 before use by the surgeon. This requirement stems from the fact that a strict requirement during surgical procedures is the sterility of the environment around the patient. Any equipment and personnel in and around the patient must adhere to these strict sterility standards to ensure no diseases are transferred to the patient through their open wounds. This results in the application of harsh but effective sterilization methods to equipment used directly on or within the vicinity of the surgical site of interest. The most common sterilization method used presently in hospitals is autoclaving. This method involves exposing all equipment to steam under high temperature and pressure. Given the pressures and temperatures in this process can reach up to 40 psi and 375° F., this method can be problematic for any materials without the required structural integrity.

Since the example of the surgical glove interface 500 being integrated below or underneath a surgical glove results in the surgical glove interface 500 not being in direct contact with the patient, the sterilization requirement can be omitted. Alternatively, since both the example of the surgical glove interface 500 being integrated on top of a surgical glove and into a surgical glove may result in some of the parts being exposed to the area around the patient when the glove is in use, these surgical glove interfaces 500 may have to be sterilizable.

In the case of the autoclave example mentioned above, surgical glove interfaces 500 must be able to withstand 40 psi and 375° F. Since the surgical glove interfaces 500 may involve the use of electronics for functionality, the electronic components must be either shielded from the mentioned environmental factors or able to withstand these factors. Some examples of shielding components that can be used in conjunction with electronics are provided by Schott North America Inc.™. Particular considerations for the surgical glove interface 500 being integrated into a surgical glove design is the sterilization barrier and methods of manufacturing such a connection. The sterilization barrier refers to the connection of two materials and how that connection is ensured to be sterile and preventative of disease passing from one side of the barrier to the other. In one example, this may be a barrier between a button and the surgical glove interface. Other requirements for sterility include ensuring the barrier of the glove does not tear.

The second row of the table 900 in FIG. 9 refers to the structural integrity of the glove that must adhere to particular standards to be utilized in the surgical suite. This requirement is a result of sterility requirement, explained above. To preserve sterility the glove must not tear from regular use, the specific requirements of which are well documented and known to those skilled in the relevant arts. For example, the minimum tensile strength of synthetic rubber gloves may be 17 MPa and the minimum ultimate elongation may be 650%. Therefore, when designing the surgical glove interface 500 described herein, the mentioned mechanical properties may adhere to the known minimum requirements. Another result of these requirements is that any surgical glove interface 500 should not cause the mechanical properties of the glove with which it is used to be jeopardized. Example considerations may include smooth device edges to prevent catching of the glove on the edges resulting in accidental tearing.

The third row of the table 900 in FIG. 9 refers to the desire to conserve the dexterity of the surgeon. During surgical procedures, minimizing the hindrance of a surgeon's dexterity when using his surgical tools is a high priority. Various design parameters can be implemented to meet this priority with respect to the surgical glove interface 500, disclosed herein. Example parameters which optimize dexterity of the surgeon when utilizing the surgical glove interface 500 are provided as follows. Firstly, the surgical glove interface 500 may provide the surgeon functionality with his hands that most closely mimics the surgeon's functionality with his hands without the use of the surgical glove interface 500 (such as making the glove very thin and light). This parameter allows the surgeon greater comfort in movement and maneuverability of his hands without having to adjust his motor control for less flexibility and also allows the surgeon the greatest use of his touch sense to maneuver any tissues and surgical instruments he may be operating with. Secondly, the surgical glove interface 500 may provide improved grip, which increases the surgeon's ability to precisely maneuver any surgical instruments and tissues the surgeon operates on, for example loss of grip due to fluid on the hands such as sweat, blood, or other bodily fluids. Presently manufactured surgical gloves address these needs by providing gloves made of a material to minimize thickness, maximize flexibility, maximize grip, and adhere to the structural integrity required to resist active wear and tear over a single surgery. Thinner gloves allow for a better sense of feel as there is less material between the hands and the object and therefore perturbations of the surface of the glove are more easily transferred through the material. Choosing a glove with the correct material composition may allow the glove to be flexible enough so as to not restrict the surgeon's movement, have a stronger grip depending on its surface friction, and adhere to structural integrity requirements to not endanger the sterility barrier by accidental tearing through regular use.

Given that the fingers are the part of the hand most associated with dexterity when utilizing surgical tools to perform operations, it would also be advantageous to provide a surgical glove interface 500 that leaves the finger segments of the glove unobstructed, as discusses below in connection with FIGS. 10 and 11.

The fourth row of the table 900 in FIG. 9 refers to the desire to reduce the amount of fatigue experienced by the surgeon during a surgical operation. This consideration in the design of the surgical glove interface 500 disclosed herein may refer to the weight of the glove in that heavier gloves would result in the surgeon's arms becoming fatigued faster as compared to using a glove of lesser weight. While including a device on the surgical glove interface 500 will definitively increase the weight of the surgical glove interface 500, minimizing this weight to not significantly increase the weight from the presently used gloves would result in an optimal outcome of the design.

The fifth row of the table 900 in FIG. 9 refers to the desire to maximize the tactical feel of any switches located on the surgical glove interface 500. Given the surgical glove interface 500 disclosed herein may involve the use of touch for actuation of the switches 502, 510, 515, 520, tactile feel becomes an important consideration when designing a surgical glove interface 500 for use in the surgical suite. In general, the surgeon should be able to maneuver and utilize the switches 502, 510, 515, 520 with minimal effort and maximum accuracy. To minimize effort, the switches 502, 510, 515, 520 may be placed such that the switches 502, 510, 515, 520 are easy to access from the bimanual manipulation position and easy to actuate without requiring more force than necessary to ensure purposeful actuation. Meeting the mentioned design considerations would not only allow for greater ergonomic ease in utilization of the switches 502, 510, 515, 520, but would also reduce the fatigue of the surgeon by requiring less force application.

The sixth row of the table 900 in FIG. 9 refers to the consideration of the use of multiple tools during a surgery. During a surgical procedure, a surgeon typically utilizes a multiplicity of instruments which involve a multiplicity of hand placements. Some examples are endosurgical forceps, resection devices, tissue maneuvering devices, and surgical drilling devices. Where the surgical forceps would require the surgeon to hold a device in a similar manner to holding a pair of scissors the surgical drill would require the surgeon to grasp the handle with his entire palm. From these two hand placement examples, it is apparent that the surgical glove interface 500 may aim to compensate for the use of multiple devices without hindering the surgeon's ability to utilize such devices.

In addition, when in use the surgical glove interface 500 may be used to control multiple devices so as the surgeon changes devices the UI configuration of the surgical glove interface 500 changes to support each device. This consideration may result in the surgical glove interface 500 being designed such that all of the required devices are supported, as well as having a layout to accommodate all the instruments the surgical glove interface 500 would be able to control.

The seventh row of the table 900 in FIG. 9 refers to the desire to utilize a wireless connection to communicate between the surgical glove interface 500 (e.g., outputs of the switches 502, 505, 510, 515) and the medical navigation system 600, such as the systems shown in FIGS. 2, 3, and 6. During a surgical operation the surgeon needs to orient himself in the surgical suite to perform any necessary movements and actions required to assure patient trauma is minimized. If the surgical glove interface 500 is not wireless, this could lead to issues such as the surgeon being bound to a particular zone. In most cases this binding wouldn't be an issue but in cases were irregularities occur and emergency procedures come into play this may present a detrimental constraint. Therefore, one aspect of the present description includes the surgical glove interface 500 being compatible with a wireless communicator.

The table provided in FIG. 9 indicates which features are desirable for each of the three examples where the surgical glove interface 500 may be integrated: (a) on top of a presently used surgical glove (e.g., "over glove" shown in FIG. 9, (b) into a surgical glove ("integrated into glove" shown in FIG. 9, or (c) below or underneath a surgical glove ("under glove" shown in FIG. 9). Some examples of these are discussed below.

In one example, an interface component is provided for use with a first glove and a medical equipment component. The interface component comprises a plurality of switches located on the first glove. Each of the plurality of switches provides a control signal to the medical equipment component. The interface component may further comprise a controller coupled to the plurality of switches; a power supply module coupled to the controller; and a wireless communications interface coupled to the controller in communication with a wireless interface of the medical equipment component.

Figure 10:
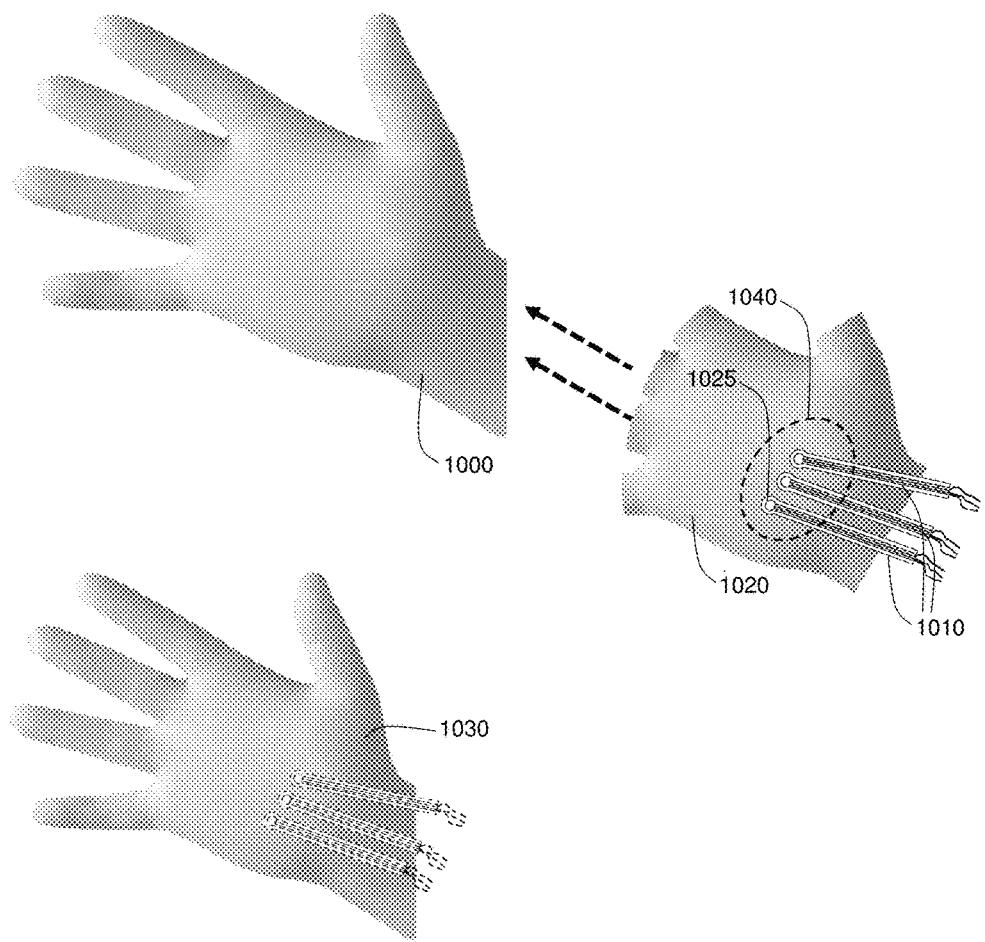
FIG. 10 shows another exemplary surgical glove interface according to aspects of the present disclosure.

Referring to FIG. 10, an example surgical glove interface (e.g., also referred to generally as an interface component), such as the surgical glove interface 500, to be applied to a surgical glove 1000, where the interface is positioned below or underneath the surgical glove 1000 is shown. The interface component may be used with a first glove 1020 with an integrated user interface device 1040. In one example, the first glove 1020 may be fingerless and the user interface device 1040 may be positioned on the palm. A benefit of the first glove 1020 being below or underneath a second glove such as the surgical glove 1000 is that the surgical glove 1000 performs as an outer barrier to protect the patient and the surgical glove 1000 already adheres to the required structural integrity standards needed to be used in the surgical suite. The first glove 1020 may be made of a flexible elastic material, such as spandex, a polyester cotton blend, latex, neoprene, vinyl, nitrile rubber, or other applicable polymers and materials. However, any other suitable material may be used to meet the design criteria of a particular application. Spandex would allow the first glove 1020 to conform to the needs for dexterity as spandex does not constrain the surgeon's hand movements. In the example where the first glove 1020 is fingerless, the surgeon's fingers, which are primarily used to handle the surgical instruments, may not incur any significant reduction in dexterity. The user interface device 1040 may be formed of a plurality of switches 1025 (e.g., the switches 502, 505, 510, 515 shown in FIG. 5), where each of the plurality of switches 1025 may provide a control signal to a medical equipment component, such as the medical navigation systems shown in FIGS. 2, 3, and 6. In one example, the plurality of switches 1025 may include flexible pressure sensors that may be configured to actuate at a given minimum pressure and may be used in either binary or variable switch modes. Using flexible pressure sensors may not constrain the surgeon's movements allowing the surgeon to maintain his dexterity.

The plurality of switches 1025 may also be lightweight, thereby minimizing fatigue of the surgeon's arms and may be autoclavable allowing the switches 1025 to be sterilized. The switches 1025 may be thin in addition to being flexible, which reduces the likeliness of the switches 1025 catching the second surgical glove 1000 and potentially causing unsafe tears. An example of a suitable sensor for use as the switches 1025 is the FlexiForce® Model HT201. For tactility, the flexible sensors may be designed similar to the buttons 502, 505, 510, and 515 shown in FIG. 5, where each button has a unique raised pattern that can be felt through the surgical glove 1000 by the surgeon. In other words, the plurality of switches 1025 may each have a textured surface for tactile identification by a wearer of the first glove 1020. In another example, the second surgical glove 1000 to be worn over the surgical glove interface 500 (e.g., the first glove 1020 including the user interface device 1040) may be designed with additional slack and less material specifically positioned where the flexible switches 1025 would be located during use.

The interface component may also include a controller (e.g., the controller 622) coupled to the plurality of switches 1025 (e.g., switches 615), a power supply module (e.g., the power supply module 625) coupled to the controller, and a wireless communications interface (e.g., the interface 605) coupled to the controller in communication with a wireless interface (e.g., the interface 610) of the medical equipment component (e.g., the medical navigation system 600). In another example, the plurality of switches 1025 may each be coupled to the medical equipment component with physical wire 1010, which may make it unnecessary for the first glove 1020 to have a controller, power supply, and wireless communications interface integrated therein. The plurality of switches 1025 may be in a location on a palm of the first glove 1020 that is accessible to fingers of a hand that is insertable into the first glove 1020. The plurality of switches may alternatively be located either at the back of the first glove 1020 and or the side of the first glove 1020. Alternatively, the wires 1010 may lead to a controller (e.g., the controller 622), a power supply module (e.g., the power supply module 625) coupled to the controller, and a wireless communications interface (e.g., the interface 605) that is placed in a location away from the first glove 1020, such as attached to an arm or belt of the surgeon.

Figure 11:
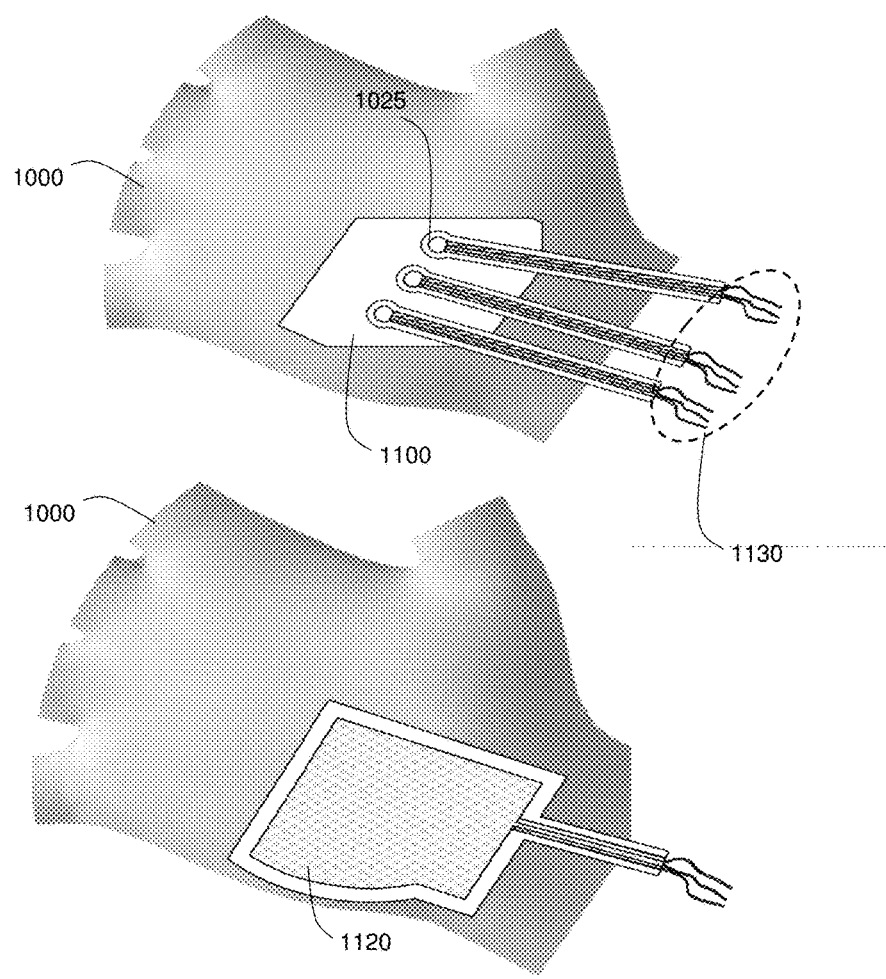
FIG. 11 shows yet another exemplary surgical glove interface according to aspects of the present disclosure.

Referring now to FIG. 11, another example of the surgical glove interface (e.g., an interface component) shown in FIG. 10 is shown. In the example shown in FIG. 11, a thin, semi-rigid or substantially rigid board 1100 may be placed underneath the switches 1025 to help more evenly distribute the force over the palm resulting in less compression to the skin of the hand and more force transfer to the switches 1025. The use of the board 1100 may also aid in increasing the tactility of the switches 1025. To compensate for the use of multiple instruments, a detection system could be used to identify which medical instruments were being used. Based on the instrument, the interface component may be configured with new switch outputs and consequent functionality including being in a disabled state to allow for manual use of tools such as a drill. Methods of detecting which instruments would be in use include using radio frequency ID (RFID) tags on the instruments for detection, as well as optical detection methods such as active markers on the instruments. Since a wireless connection may be used between the interface component and the medical navigation system (e.g., the systems shown in FIGS. 2, 3, and 6), a Bluetooth dongle may be coupled to the interface component and used to transmit the output of the interface component. The dongle may be located on the surgeon anywhere under the sterile barrier and attached to the interface component via the wires 1130 shown in FIG. 11.

Alternate embodiments of the interface component include the interface component including the first glove 1020 being placed on top of the second surgical glove 1000. An example of this can be seen in FIG. 11, where the interface component includes a flexible touch pad 1120. In another example, surgical glove interface 500 shown in FIG. 5, employs the buttons 502, 505, 510, and 515.

An additional embodiment integrates the interface component including the first glove into a surgical glove (e.g., the first glove is, in fact, a surgical glove itself—shown as 1030 in FIG. 10) where any of the features discusses above may be built right into the material of a presently used or specially designed surgical glove interfaces so they come as a single piece.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A wearable interface for use a first medical equipment, the interface comprising:
   at least one finger-activatable switch for providing a control signal to control at least the first medical equipment;
   wherein, when the interface is worn on a single hand of a wearer, the at least one switch is in a location corresponding to a palm of the single hand that is accessible to fingers of the single hand to enable easy access by at least two fingers of the single hand, while enabling the wearer to manipulate a second medical equipment held in the single hand in a bimanual procedural position.

2. The interface of claim 1, wherein the interface is adaptable for controlling multiple tools in a single surgical procedure.

3. The interface of claim 1, wherein:
   the first medical equipment is a pair of forceps, and the at least one switch is activatable to provide a control signal to control the forceps for cauterization;
   the first medical equipment is a resection device, and the at least one switch is activatable to provide a control signal to control the resection device for suction, tissue removal or tissue manipulation;
   the first medical equipment is an irrigation tool, and the at least one switch is activatable to provide a control signal to control the irrigation tool for irrigation;
   the first medical equipment is a drill, and the at least one switch is activatable to provide a control signal to control activation of the drill or speed of the drill; or
   the first medical equipment is a Raman probe, and the at least one switch is activatable to provide a control signal to control the Raman probe to acquire data.

4. The interface of claim 1, wherein the first medical equipment is a navigation system, and wherein the at least one switch is activatable to interface with a graphical user interface (GUI) of the navigation system.

5. The interface of claim 1, wherein the first medical equipment is an imaging device, and wherein the at least one switch is activatable to provide a control signal to control the imaging device to acquire an image.

6. The interface of claim 1, wherein the first medical equipment is an automated arm, and wherein the at least one switch is activatable to provide a control signal to control the automated arm to mobilize.

7. The interface according to claim 1, wherein the at least one switch includes a plurality of switches and the interface further comprises:
   a controller coupled to the plurality of switches;
   a power supply module coupled to the controller; and
   a wireless communications interface coupled to the controller in communication with a wireless interface of the first medical equipment.

8. The interface according to claim 7, wherein the wireless communications interface is selected from the group consisting of Bluetooth, Wifi, and iRDA.

9. The interface according to claim 7, wherein the power supply module includes a rechargeable battery.

10. The interface according to claim 7, wherein the interface further includes an output device coupled to the controller for providing an output, the output device being configured to provide at least one of: a visual alert, an audible alert, or a tactile alert.

11. The interface according to claim 1, wherein the at least one switch is coupled to the first medical equipment with physical wire.

12. The interface according to claim 1, further comprising at least one other switch, wherein, when the interface is worn on the single hand, the at least one other switch is in a location corresponding to at least one of a back of the single hand or a side of the single hand.

13. The interface according to claim 1, wherein the interface is integrated into a surgical glove.

14. The interface according to claim 1, wherein the at least one switch includes a plurality of switches and each switch is selected from the group consisting of a joystick, a touchpad, a button, and a slider.

15. The interface according to claim 1, wherein the at least one switch includes a plurality of switches and the plurality of switches each has a different textured surface for tactile identification by the wearer of the first glove.

16. The interface according to claim 1, wherein the at least one switch includes a plurality of switches and the plurality of switches is selected from the group consisting of a binary switch, a variable switch, and a flexible pressure sensor.

17. A medical navigation system comprising:
a controller;
at least a first medical equipment coupled to receive signals from the controller;
a wearable interface for interfacing with the controller, the wearable interface including:
at least one finger-activatable switch wearable on a single hand for providing a control signal to the controller;
wherein, when the wearable interface is worn on a single hand of a wearer, the at least one switch is in a location corresponding to a palm of the single hand that is accessible to fingers of the single hand to enable easy access by at least two fingers of the single hand, while enabling the wearer to manipulate a second medical equipment held in the single hand in a bimanual procedural position;
wherein the controller is configured to relay the control signal from the wearable interface to control at least the first medical equipment.

18. The system of claim 17, further comprising a third medical equipment, wherein the wearable interface is configured to provide control signals for controlling the first medical equipment and the third medical equipment during a single surgical procedure.

19. The system of claim 17, wherein
the first medical equipment is a pair of forceps, and the at least one switch is activatable to provide a control signal to control the forceps for cauterization;
the first medical equipment is a resection device, and the at least one switch is activatable to provide a control signal to control the resection device for suction, tissue removal or tissue manipulation;
the first medical equipment is an irrigation tool, and the at least one switch is activatable to provide a control signal to control the irrigation tool for irrigation;
the first medical equipment is a drill, and the at least one switch is activatable to provide a control signal to control activation of the drill or speed of the drill;
the first medical equipment is a Raman probe, and the at least one switch is activatable to provide a control signal to control the Raman probe to acquire data;
the first medical equipment is an imaging device, and the at least one switch is activatable to provide a control signal to control the imaging device to acquire an image; or
the first medical equipment is an automated arm, and the at least one switch is activatable to provide a control signal to control the automated arm to mobilize.

20. The system of claim 17, wherein the controller is configured to cause an output device to display a graphical user interface (GUI), and wherein the at least one switch is activatable to interface with the GUI.

* * * * *